(12) United States Patent
Magna et al.

(10) Patent No.: US 7,115,774 B2
(45) Date of Patent: Oct. 3, 2006

(54) PROCESS FOR CARBONYLATING ALCOHOLS, EMPLOYING A CATALYST BASED ON RHODIUM OR IRIDIUM IN A NON-AQUEOUS IONIC LIQUID, WITH EFFICIENT CATALYST RECYCLING

(75) Inventors: Lionel Magna, Rueil Malmaison (FR); Helene Olivier-Bourbigou, Rueil Malmaison (FR); Stephane Harry, Montesson (FR); Dominique Commereuc, Meudon (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 233 days.

(21) Appl. No.: 10/443,116

(22) Filed: May 22, 2003

(65) Prior Publication Data

US 2004/0059153 A1    Mar. 25, 2004

(30) Foreign Application Priority Data

May 23, 2002   (FR) .................................. 02 06317

(51) Int. Cl.
*C07C 51/12* (2006.01)
(52) U.S. Cl. ...................... 562/519; 562/517
(58) Field of Classification Search ............... 562/512, 562/517, 519, 606, 607; 560/206, 207; 502/300, 502/325, 326
See application file for complete search history.

(56) References Cited

U.S. PATENT DOCUMENTS 4,366,259 A * 12/1982 Knifton et al. ............. 518/700
6,211,405 B1 * 4/2001 Cheung et al. ............. 562/519

FOREIGN PATENT DOCUMENTS

| EP | 0338730 | 10/1989 |
| EP | 0976711 | 2/2000 |
| GB | 2029409 | 3/1980 |

* cited by examiner

*Primary Examiner*—Thurman K. Page
*Assistant Examiner*—Karl Puttlitz
(74) *Attorney, Agent, or Firm*—Millen, White, Zelano & Branigan, P.C.

(57) ABSTRACT

In a process for liquid phase carbonylation of alcohols by carbon monoxide, the carbonylation reaction is carried out in a reaction zone at a temperature of 50° C. to 150° C. at a pressure in the range 0.5 MPa to 20 MPa in the presence of at least one catalyst comprising at least one rhodium and/or iridium complex and a halogenated promoter in at least one non-aqueous ionic liquid comprising at least one salt with general formula $Q^+A^-$, in which $Q^+$ represents a quaternary ammonium and/or a quaternary phosphonium cation, said salt having a melting point of less than 90° C.; the non-aqueous ionic liquid containing at least the major portion of the catalyst is separated; and the separated non-aqueous ionic liquid containing at least the major portion of the catalyst is returned to the reaction zone.

27 Claims, 1 Drawing Sheet

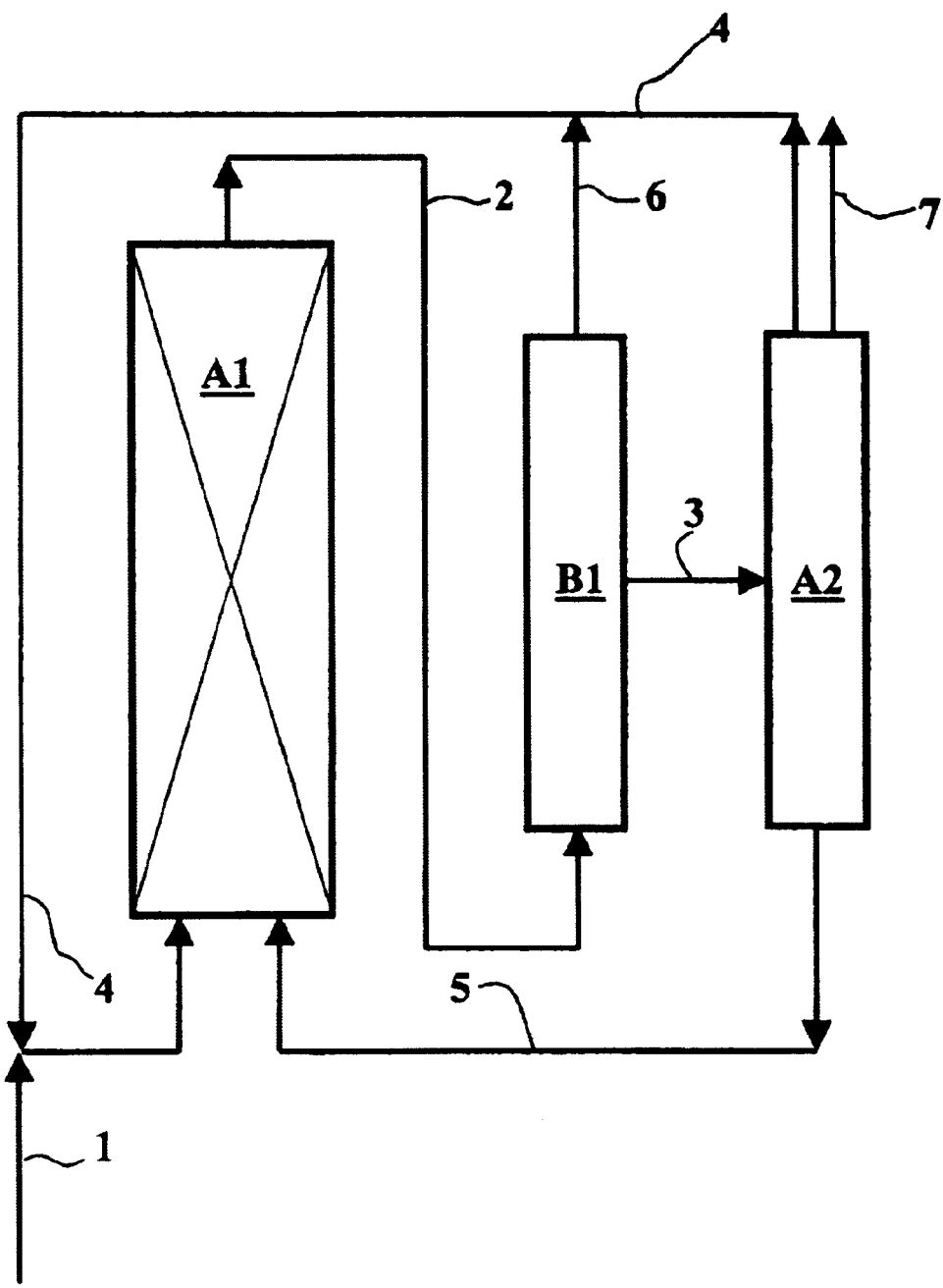

PROCESS FOR CARBONYLATING ALCOHOLS, EMPLOYING A CATALYST BASED ON RHODIUM OR IRIDIUM IN A NON-AQUEOUS IONIC LIQUID, WITH EFFICIENT CATALYST RECYCLING

BACKGROUND OF THE INVENTION

1. Field of the Invention

The present invention relates to a process for carbonylating alcohols by means of a rhodium or iridium based catalyst in the presence of a halide used as a promoter, carried out in an ionic liquid medium with efficient catalyst recycling. The homogeneous system obtained at the end of the reaction is distilled. The distillation residue is constituted by the catalyst dissolved in a non-aqueous ionic liquid. Said ionic liquid comprises at least one quaternary ammonium and/or phosphonium cation $Q^+$ and at least one anion $A^-$. The catalyst comprises at least one complex of rhodium or iridium and the promoter is constituted by at least one halide.

Carbonylation of alcohols, in particular methanol, is a reaction of major industrial importance in the manufacture of acetic acid used in a wide variety of applications. That product is directly involved in the manufacture of vinyl acetate and acetic anhydride and can be used as a reaction solvent in the production of terephthalic acid.

2. Description of the Prior Art

Many references deal with the production of acetic acid by methanol carbonylation. Examples that can be cited are the articles by BASF at the end of the 1960s (*Hydrocarbon Processing*, November 1966, vol. 45, n° 11, p 141 and *Hydrocarbon Processing*, November 1973, p 92) which describe the methanol carbonylation reaction under very severe conditions (60 MPa, 230° C.) in the presence of a complex based on cobalt promoted by an iodine derivative. In the 1970s, Monsanto commercialized an improved process (Monsanto (1973), U.S. Pat. No. 3,769,329) which functions under much milder temperature and pressure conditions (3 to 4 MPa, 180–220° C.) in the presence of a rhodium based complex promoted by methyl iodide. That process is distinguished by a very high yield of acetic acid (99%) linked to the presence of a high concentration of water in the reaction mixture. In 1980, Hoechst-Celanese improved the Monsanto process by adding a promoter based on lithium iodide or sodium iodide (Hoechst Celanese, Corp (1991), U.S. Pat. No. 5,001,259), which considerably reduced the concentration of water necessary in the Monsanto process and thus limited problems with the formation of by-products by reducing the "water gas shift" side reaction. Finally, in 1996, BP Chemicals sold a process based on iridium (Cativa™) comparable with the Monsanto process with a low water concentration (Chem Br 32 (1996) 7 and Chem Ind (London) 483 (1996)). That process was a considerable improvement over the earlier processes, for example in increasing the reaction rates, reducing liquid by-products and increasing the yield with respect to carbon monoxide.

The majority of said processes use homogeneous catalysts dissolved in an organic phase constituted by reagents and products, which sometimes renders separation complex and expensive.

SUMMARY OF THE INVENTION

It has now been discovered that, in the alcohol carbonylation reaction catalyzed by rhodium or iridium complexes, the use of a non-aqueous ionic liquid comprising at least one quaternary ammonium and/or phosphonium cation $Q^+$ and at least one anion $A^-$, liquid at a temperature of less than 90° C., substantially improves recycling of the metal in the ionic liquid. The homogeneous mixture at the end of the reaction can be distilled directly. The low vapour tension of the ionic liquid and its high thermal stability allows the stabilized catalyst that is kept soluble in the ionic liquid to be recovered from the bottom of the distillation column. At the end of this distillation step, the ionic liquid phase containing the catalyst can be re-used.

BRIEF DESCRIPTION OF THE DRAWINGS

The FIGURE shows a diagrammatic flowsheet of the process according to the invention, schematically representing the apparatus used to implement it.

DETAILED DESCRIPTION OF THE INVENTION

More precisely, the present invention aims to provide a process for liquid phase carbonylation of alcohols by carbon monoxide, characterized in that it comprises:

carrying out the carbonylation reaction in a reaction zone at a temperature of 50° C. to 150° C. at a pressure in the range 0.5 MPa to 20 MPa in the presence of at least one catalyst comprising at least one rhodium and/or iridium complex and a halogenated promoter in at least one non-aqueous ionic liquid comprising at least one salt with general formula $Q^+A^-$, in which $Q^+$ represents a quaternary ammonium and/or a quaternary phosphonium cation, said salt having a melting point of less than 90° C.;

withdrawing an effluent from the reaction zone and separating from the effluent the non-aqueous ionic liquid containing in dissolved form substantially all rhodium and/or iridium values in the effluent; and recycling at least partly the resultant separated non-aqueous ionic liquid to the reaction zone.

Without wishing to be bound by any particular theory, it can be considered that under the carbonylation reaction conditions, under carbon monoxide pressure, the catalyst is present for example, when the precursor is an iodide, mainly in the form of the complex $[Rh(CO)_2I_2]^-$ (if the precursor is based on rhodium) or $[Ir(CO)_2I_2]^-$ (if the precursor is based on iridium) which, considering its ionic nature, remains highly soluble and stable in the molten salt phase during and after distillation, despite the absence of any additional ligand such as a phosphine or a phosphate, intended to increase the stability of the complex during and after distillation.

The non-aqueous ionic liquid is selected from the group formed by liquid salts with general formula $Q^+A^-$ in which $Q^+$ represents a quaternary ammonium and/or a quaternary phosphonium and $A^-$ represents any anion that is capable of forming a liquid salt at low temperatures, i.e., below 90° C. and advantageously at most 85° C., and preferably below 50° C. Preferred anions $A^-$ are nitrate, sulfate, phosphate, acetate, halogenoacetates, tetrafluoroborate, tetrachloroborate, tetraalkylborates, tetraarylborates, hexafluorophosphate, hexafluoroantimonate, fluorosulfonate, alkylsulfonates, perfluoroalkysulfonates, bis(perfluoroalkylsulfonyl)amides and arenesulfonates, the latter optionally being substituted with halogenated or halogenoalkyl groups. With the same condition that the salt is liquid below 90° C., the anion $A^-$ can also be a halide, for example an iodide. In this case, it is important that the ionic liquid acts as the solvent and constitutes more than 20% by weight of the catalyst system.

The quaternary ammonium and/or phosphonium cation(s) $Q^+$ preferably has/have general formulae $NR^1R^2R^3R^{4+}$ and $PR^1R^2R^3R^{4+}$, or general formulae $R^1R^2N{=}CR^3R^{4+}$ and $R^1R^2P{=}CR^3R^{4+}$ in which $R^1$, $R^2$, $R^3$ and $R^4$, which may be identical or different, represent hydrogen (with the exception of the cation $NH_4^+$ for $NR^1R^2R^3R^{4+}$); preferably, a single substituent represents hydrogen, or hydrocarbyl residues containing 1 to 30 carbon atoms, for example alkyl groups that may or may not be saturated, cycloalkyl or aromatic groups, or aryl or aralkyl groups that may be substituted, containing 1 to 30 carbon atoms. The ammonium and/or phosphonium cations can also be derived from nitrogen-containing and/or phosphorus-containing heterocycles containing 1, 2 or 3 nitrogen and/or phosphorus atoms in which the cycles are constituted by 4 to 10 atoms, preferably 5 or 6 atoms.

The quaternary ammonium and phosphonium cations may also satisfy the following formulae respectively:

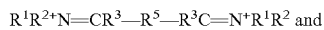

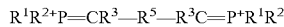

in which $R^1$, $R^2$ and $R^3$, which may be identical or different, are as defined above, and $R^5$ represents an alkylene or phenylene radical. Among groups $R^1$, $R^2$, $R^3$ and $R^4$, the radicals may be methyl, ethyl, propyl, isopropyl, butyl, secondary butyl, tertiary butyl, amyl, methylene, ethylidene, phenyl or benzyl; $R^5$ may be a methylene, ethylene, propylene or phenylene group.

The ammonium and/or phosphonium cation $Q^+$ is preferably selected from the group formed by N-butylpyridinium, N-ethylpyridinium, pyridinium, 3-ethyl-1-methylimidazolium, 3-butyl-1-methylimidazolium, 3-hexyl-1-methylimidazolium, 3-butyl-1,2-dimethylimidazolium, diethylpyrazolium, N-butyl-N-methylpyrrolidinium, trimethylphenylammonium, tetrabutyl-phosphonium and tributyl-tetradecylphosphonium.

Examples of salts that can be employed in the invention that can be cited are N-butylpyridinium hexafluorophosphate, N-ethyl pyridinium tetrafluoroborate, pyridinium fluorosulfonate, 3-butyl-1-methylimidazolium tetrafluoroborate, 3-butyl-1-methylimidazolium hexafluoroantimonate, 3-butyl-1-methylimidazolium hexafluorophosphate, 3-butyl-1-methyl-imidazolium trifluoroacetate, 3-butyl-1-methylimidazolium trifluoromethylsulfonate, 3-butyl-1-methylimidazolium bis(trifluoromethylsulfonyl)amide, trimethylphenylammonium hexafluoro-phosphate and tetrabutylphosphonium tetrafluoroborate. These salts may be used alone or as a mixture.

Any source of rhodium or iridium which will react with carbon monoxide in the reaction medium to produce a rhodium-carbonyl or iridium-carbonyl complex can be used in the context of the present invention. The rhodium and iridium catalyst precursors are, for example, selected from the group formed by their salts such as halides, acetylacetonates, carboxylates and in particular the formate or acetate, carbonyl complexes such as rhodium dicarbonyl acetylacetonate, and carbonyl clusters. The choice of precursor metallic compound is not critical, but halides are preferably used.

All halides or halogenated compounds used as the promoter or catalyst precursor may be suitable for the system of the present invention. However, we prefer those containing iodine and bromine. Possible promoter agents are those with formula $RX_n$, in which n is in the range 1 to 3, R is an alkyl or aromatic group and X is a chlorine, bromine or iodine atom (for example $CH_3I$, $C_6H_5Br$, $CH_3CH_2I$, $ICH_2CH_2I$, etc). It is also possible to use promoters with formulae $X_2$ or $X_3^-$, in which X is an iodine, chlorine or bromine atom (for example $Br_2$, $I_2$, $I_3^-$, etc). Acids with formula HX can also be used as promoters suitable for use in the present invention (for example HI, HBr or HCl).

The catalyst composition is obtained by mixing the ionic liquid with the rhodium and/or iridium compound and the halide (promoter), in any manner. It is also possible to dissolve the transition metal compound in an organic solvent in advance. This organic solvent can be added in a large excess and used as the reaction solvent.

The reaction rate depends on the concentration of catalyst in the system. The concentration of rhodium and/or iridium is advantageously in the range 0.1 mmoles per liter to 5 moles per liter, preferably in the range 1 mmole to 1 mole per liter, or even in the range 10 to 500 mmoles per liter. The mole ratio between the halogenated promoter and the rhodium compound is in the range 0.1:1 to 1000:1, preferably in the range 1:1 to 500:1.

Examples of starting materials preferably used for the carbonylation reaction of the present invention are aliphatic alcohols containing 1 to 20 carbon atoms and aromatic alcohols containing 6 to 20 carbon atoms such as methanol, ethanol, propanol, isopropanol, butanols, pentanols, benzyl alcohol, 1-phenyl ethanol and its derivatives, phenol and hexanols, as well as higher alcohols such as decanols and their isomeric forms. However, the preferred starting material is an alcohol. As an example, if acetic acid or its derivatives is/are to be obtained, the starting substance can be methyl alcohol or its derivatives, such as dimethyl ether, methyl acetate, methyl iodide and/or combinations of these substances.

In accordance with the present invention, the carbonylation reaction is preferably carried out under a carbon monoxide pressure in the range 1 to 10 MPa.

The catalytic alcohol carbonylation reaction can be carried out in a closed system, in a semi-open system or in a continuous system with one or more reaction stages. In a continuous implementation, the effluent from the pressurized reactor is transferred into a depressurizing chamber in which it is depressurized to a pressure which can be as low as 0.5 MPa, at a temperature of at most 100° C. and preferably less than 60° C. The contents of the depressurizer are then distilled.

At the outlet from the distillation zone, at least a portion of the non-aqueous ionic liquid phase containing almost all of the catalyst is returned to the reactor, the other portion being treated to eliminate the very small quantity of catalyst decomposition residues and any heavy by-products.

An apparatus for carrying out the carbonylation process as defined in the above description, comprises:
at least one reactor A1;
at least one depressurization vessel ("depressurizer") B1;
and at least one distillation chamber A2 to separate the reaction products from the ionic liquid containing at least the catalyst, which is recycled to reactor A1; and also:
at least one line 2 for transferring the effluent from the reactor to the depressurizer B1;
at least one line 2 for transferring the effluent from the reactor to the depressurizer B1;
at least one line 3 for sending the mixture of the organic effluent and the ionic solvent contained in the depressurizer B1 to the distillation chamber A2;

at least one line 6 for returning gas from the depressurizer B1 to the reactor A1;

at least one line 5 for returning the flash residue containing at least the ionic liquid and the catalyst separated in A2 to the reactor A1.

The apparatus also comprises:

in the separation section, at least one column A2 for separating out the crude reaction products from the unreacted alcohol to be carbonylated and the promoter agent;

and also:

at least one line 4 for recycling the unreacted alcohol to be carbonylated and promoter separated in column A2 to the reactor A1;

at least one line 7 for sending the products leaving from the head of the column A2 to the remainder of the product fractionation train.

The process and apparatus of the invention will be better understood from the description below, made with reference to FIG. 1.

In FIG. 1, the reaction is carried out in the reactor A1 in the presence of the feed to be carbonylated, which can be introduced via a line 1, of a transition metal compound(s), carbon monoxide, which can be introduced via line 1, and in the presence of at least one non-aqueous ionic liquid and the halogenated promoter. The ionic liquid can be introduced into the reactor at the start of the reaction. Optionally, fresh ionic liquid can be injected into the reactor A1 during the reaction and used ionic liquid can be withdrawn from A1 (the means for injecting and withdrawing the ionic liquid are not shown in FIG. 1).

The heat of reaction is removed by techniques that are known to the skilled person and which are not shown in FIG. 1.

At the outlet from the reaction section, the reactor effluent is sent via line 2 to at least one depressurizer B1 in which the pressure is reduced. Stirring can be maintained in B1 either by mechanical means or by any other suitable means. The gas released by the depressurization escapes via line 6 and is returned to the reactor A1 after recompression.

The effluent from depressurizer B1 is sent to a distillation column A2 via a line 3. In this column A2, unreacted alcohol to be carbonylated and a portion of the halogenated promoter are separated overhead from the carbonylation products. The alcohol and the halogenated promoter can be recycled to reactor A1 via line 4. The crude reaction products collected at A2 are sent to a specific fractionation train (not shown) via line 7.

At the foot of the column A2, the polar phase containing at least the ionic liquid and the catalyst is recovered and sent to the reactor A1 via a line 5.

The following examples illustrate the invention without limiting its scope.

EXAMPLE 1

The carbonylation reaction was carried out in a 100 ml stainless steel autoclave with a vitrified coating provided with a jacket for regulating the temperature by circulation of a heat transfer fluid and provided with an efficient magnetic stirring system. A solution containing 200 mg of $RhCl_3.3H_2O$ (0.76 mmoles of rhodium), 5 ml of iodomethane, 5 ml of 3-butyl-1-methylimidazolium bis(trifluoromethylsulfonyl) amide [BMI][$Tf_2N$] and 13 ml of methanol were introduced into the autoclave which had been purged of air and moisture and placed under 1 atmosphere of carbon monoxide. The carbon monoxide pressure was increased to 3 MPa, the temperature was increased to 130° C. and stirring was commenced. After 2 hours of reaction, the carbon monoxide inlet was closed and the reactor was rapidly cooled to 25° C. After removal from the autoclave, the effluent was homogeneous, single-phased and red in colour.

The whole system was introduced into a flash distillation assembly. The distillate was in the form of a practically colourless homogeneous liquid and the flash residue was in the form of a clear bright red homogeneous liquid. This coloration denotes the presence of the ion $(Rh(CO)_2I_2)^-$ dissolved in the ionic liquid. Gas chromatographic analysis of the distillate and weighing the unflashed residues (ionic liquid+rhodium) provided the material balance of the reaction. The methanol conversion was 99.6% by weight. The selectivity was 96.1% for acetic acid and 3.9% for methyl acetate.

EXAMPLE 2 (COMPARATIVE)

The hydroformylation reaction was carried out in the same apparatus and using the same operating procedure as that described in Example 1, with the exception that it was carried out in the absence of an ionic liquid. After withdrawal from the autoclave, the effluent was homogeneous, single-phased and red in colour.

The whole system was introduced into a flash distillation assembly. The distillate was in the form of a homogeneous red liquid and the flash residue was in the form of a black solid comprising solid metallic rhodium. Gas chromatographic analysis of the distillate and weighing the unflashed residues (rhodium) provided the material balance of the reaction. The methanol conversion was 99.6% by weight. The selectivity was 93.6% for acetic acid and 6.4% for methyl acetate.

EXAMPLE 3

The methanol carbonylation reaction was carried out in the same apparatus and using the same operating procedure as that described in Example 1, with the exception that 10 ml of distilled water was added to the system and the reaction time was increased to 3 hours. After withdrawal from the autoclave, the effluent was homogeneous, single-phased and red in colour.

The whole system was introduced into a flash distillation assembly. The distillate was in the form of a practically colourless homogeneous liquid and the flash residue was in the form of a bright red clear homogeneous liquid. This coloration denotes the presence of the ion $(Rh(CO)_2I_2)^-$ dissolved in the ionic liquid. Gas chromatographic analysis of the distillate and weighing the unflashed residues (ionic liquid+rhodium) provided the material balance of the reaction. The methanol conversion was 99.5% by weight. The selectivity was 99.5% for acetaldehyde and 0.5% for methyl acetate.

EXAMPLE 4

Recycling

The methanol carbonylation reaction was carried out in the same apparatus and using the same operating procedure as that described in Example 1. The ionic liquid phase containing the catalyst recovered at the distillation column bottom was recycled to the reactor for a fresh cycle. 5 ml of iodomethane and 13 ml of fresh methanol were added. No makeup of ionic liquid was required.

Three consecutive cycles were carried out. They are summarized in the following table:

| Cycle | Ionic liquid | Temp (° C.) | P (MPa) | Time (h) | Conversion (%) | Selectivity (%) | |
|---|---|---|---|---|---|---|---|
| | | | | | | $CH_3CO_2H$ | $CH_3CO_2CH_3$ |
| 1 | [BMI][TF$_2$N] | 130 | 3 | 2 | 99.6 | 96 | 4 |
| 2 | [BMI][TF$_2$N] | 130 | 3 | 2 | 99.5 | 96 | 4 |
| 3 | [BMI][TF$_2$N] | 130 | 3 | 2 | 99.7 | 97 | 3 |

All references in their entirety referred to herein are hereby incorporated by reference along with French priority application no. 02/06.317 filed May 23, 2002.

It is to be understood that the examples herein are meant to be only illustrative of the invention and not representative of the entire scope of the invention.

Although the invention has been described above in relation to preferred embodiments thereof, it will be readily understood by those skilled in the art that variations and modifications can be affected to those embodiments without departing from the scope and spirit of the invention.

The invention claimed is:

1. A process for carbonylating alcohols with carbon monoxide in the liquid phase, said process comprising:
   carrying out the carbonylation reaction in a reaction zone at a temperature of 50° C. to 150° C. and at a pressure in the range 0.5 MPa to 20 MPa in the presence of at least one catalyst comprising at least one rhodium and/or iridium complex and a halogenated promoter in at least one non-aqueous ionic liquid comprising at least one salt of the formula $Q^+A^-$, in which $Q^+$ represents a quaternary ammonium and/or a quaternary phosphonium cation, and A is an anion capable of forming a liquid salt below 90° C., said salt having a melting point of less than 90° C.,
   withdrawing an effluent from the reaction zone and separating from the effluent the non-aqueous ionic liquid containing in dissolved form substantially all rhodium and/or iridium values in the effluent; and
   recycling at least partly the resultant separated non-aqueous ionic liquid to the reaction zone.

2. A process according to claim 1, wherein anion $A^-$ is a halide, nitrate, sulfate, phosphate, acetate, halogenoacetate, tetrafluoroborate, terrachloroborate, hexafluorophosphate, hexafluoroantimonate, fluorosulfonate, alkylsulfonate, perfluoroalkylsulfonates, bis(perfluoroalkylsulfonyl)amide, arenesulfonate or arenesulfonate substituted with halogen or halogenoalkyl groups.

3. A process according to claim 2, wherein $A^-$ is an iodide anion and the ionic liquid constitutes more than 20% by weight of the catalyst system.

4. A process according to claim 1, wherein the quaternary ammonium and/or phosphonium cations are selected from the following formulae:

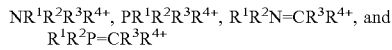

in which $R^1$, $R^2$, $R^3$ and $R^4$, which may be identical or different, each represent a hydrogen atom, the cation $NH_4^+$ being excluded, or a hydrocarbyl residue containing 1 to 30 carbon atoms.

5. A process according to claim 4, wherein the ammonium and/or phosphonium cation is derived from a nitrogen-containing and/or phosphorus-containing heterocycle containing 1, 2 or 3 nitrogen and/or phosphorus atoms, in which the cycle or cycles contain 4 to 10 atoms.

6. A process according to claim 1, wherein the quaternary ammonium and/or phosphonium cations are selected from the following formulae;

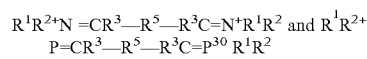

in which $R^1$, $R^2$ and $R^3$, which may be identical or different, represent a hydrogen atom or a hydrocarbyl residue containing 1 to 30 carbon atoms, and $R^5$ represents an alkylene or phenylene residue.

7. A process according to claim 1, wherein the ammonium and/or phosphonium canon is N-butylpyridinium, N-ethylpyridinium, pyridinium, 3-ethyl-1-methylimidazolium, 3-butyl-1-methylimidazolium, 3-hexyl-1-methylimidazolium, 3-butyl-1,2-dimethylimidazolium, diethylpyrazolium, N-butyl-N-methylpyrrolidinium, trimethylphenylammonium, tetrabutylphosphonium or tributyl-tetradecylphosphonium.

8. A process according to claim 1, wherein the non-aqueous ionic liquid is selected from the group consisting of N-butylpyridinium hexafluorophosphate, N-ethyl pyridinium tetrafluoroborate, pyridinium fluorosulfonate, 3butyl-1-methylimidazolium tetrafluoroborate, 3-butyl-1-methylimidazolium hexafluoroantimonate, 3-butyl-1-methylimidazolium hexafluorophosphate, 3-butyl-1-methylimidazolium trifluoromethylsulfonate, 3-butyl-1-methylimidazolium bis(trifluoromethylsulfonyl)amide, trimethylphenylammonium hexafluorophosphate and tetrabutylphosphonium tetrafluoroborate.

9. A process according to claim 1, wherein said at least one rhodium and/or iridium complex is formed from at least one rhodium and/or iridium catalyst precursor compound, and said at least one precursor is selected from the group consisting of rhodium and iridium halides, acetylacetonates, carboxylates, carbonyl complexes, and carbonyl clusters.

10. A process according to claim 1, wherein the concentration of catalyst complex in the ionic liquid is in the range 0.1 mmoles per liter to 5 moles per liter.

11. A process according to claim 1, wherein the halogenated promoter is of the formulae $RX_n$, $X_2$, $X_{3-}$, or HX, in which n is in the range 1 to 3, R is an alkyl or aromatic group and X is a chlorine, bromine or iodine atom.

12. A process according to claim 1, wherein the compound to be carbonylated is selected from aliphatic alcohols containing 1 to 20 carbon atoms and aromatic alcohols containing 6 to 20 carbon atoms.

13. A process according to claim 12, wherein the alcohol is selected from the group consisting of methanol, ethanol, propanol, isopropanol, butanols, pentanols, benzyl alcohol, 1-phenyl ethanol, phenol, hexanols, decanols, and their isomeric forms.

14. A process according to claim 1, wherein the non-aqueous ionic liquid containing substantially all of the rhodium and/or iridium values is separated by distillation.

15. A process according to claim 1, wherein the non-aqueous ionic liquid containing almost all of the separated catalyst is recycled to the carbonylation reaction.

16. A process according to claim 4, wherein at least one of $R^1$, $R^2$, $R^3$ and $R^4$ represents hydrogen.

17. A process according to claim 1, wherein said at least one catalyst does not contain a phosphine or phosphate ligand.

18. A process according to claim 1, wherein A is an anion capable of forming a liquid salt below 85° C.

19. A process according to claim 1, wherein A is an anion capable of forming a liquid salt below 50° C.

20. A process according to claim 4, wherein $R^1$, $R^2$, $R^3$ and $R^4$, which may be identical or different, are each a hydrogen atom, the cation $NH_4^{30}$ being excluded, an alkyl group containing 1 to 30 carbon atoms which is unsaturated or saturated, cycloalkyl containing up to 30 carbon atoms, aryl containing up to 30 carbon atoms, or aralkyl containing up to 30 carbon atoms.

21. A process according to claim 5, wherein the cycles of said nitrogen-containing and/or phosphorus-containing heterocycle contain 5 to 6 atoms.

22. A process according to claim 6, wherein $R^1$, $R^2$, $R^3$ and $R^4$ are each independently methyl, ethyl, propyl, isopropyl, butyl, secondary butyl, tertiary butyl, amyl, methylene, ethylidene, phenyl or benzyl and $R^5$ is methylene, ethylene, propylene or phenylene.

23. A process according to claim 1, wherein the halogenated promoter is $CH_3I$, $C_6H_5Br$, $CH_3CH_2I$, $ICH_2CH_2I$, $Br_2$, $I_2$, $I_3^-$, HI, HBr or HCl.

24. A process according to claim 1, wherein the carbonylation reaction is carried out under a carbon monoxide pressure in the range 1 to 10 MPa.

25. A process for carbonylating alcohols with carbon monoxide in the liquid phase, said process comprising,
carrying out the carbonylation reaction in a reaction zone at a temperature of 50° C. to 150° C. and at a pressure in the range 0.5 MPa to 20 MPa in the presence of at least one catalyst comprising at least one rhodium and/or iridium complex and a halogenated promoter in at least one non-aqueous ionic liquid comprising at least one salt of the formula $Q^+A^-$, in which $Q^{30}$ represents a quaternary ammonium and/or a quaternary phosphonium cation, and A is an anion capable of forming a liquid salt below 90° C. said salt having a melting point of less than 90° C.
withdrawing an effluent from the reaction zone and separating from the effluent the non-aqueous ionic liquid containing in dissolved form substantially all rhodium and/or iridium values in the effluent; and
recycling at least partly the resultant separated non-aqueous ionic liquid to the reaction zone.
wherein said process is continuous and said effluent front said reaction zone is depressurized to a pressure as low as 0.5 MPa, at a temperature of at most 100° C., before separating said non-aqueous ionic liquid.

26. A process according to claim 1, wherein said at least one catalyst comprises at least one iridium complex and a halogenated promoter in at least one non-aqueous ionic liquid comprising at least one salt of the formula $Q^+A^-$.

27. A process according to claim 1, wherein said at least one catalyst comprises at least one iridium complex and a halogenated promoter in at least one non-aqueous ionic liquid comprising at least one salt of the formula $Q^+A^-$.

* * * * *

UNITED STATES PATENT AND TRADEMARK OFFICE
CERTIFICATE OF CORRECTION

PATENT NO. : 7,115,774 B2
APPLICATION NO. : 10/443116
DATED : October 3, 2006
INVENTOR(S) : Lionel Magna It is certified that error appears in the above-identified patent and that said Letters Patent is hereby corrected as shown below:

Column 8, line 16 reads "$P^{30}$" should read --$P^{+}$--
Column 8, line 23 reads "canon" should read -- cation --
Column 9, line 15 reads "$NH_4^{30}$" should read -- $NH_4^{+}$ --
Column 10, line 9 reads "$Q^{30}$" should read -- $Q^{+}$--
Column 10, line 20 reads "front" should read -- from --
Column 10, line 25 reads "iridium" should read -- rhodium --

Signed and Sealed this

Seventeenth Day of April, 2007

JON W. DUDAS
*Director of the United States Patent and Trademark Office*